United States Patent
Hauger et al.

(10) Patent No.: US 6,741,948 B2
(45) Date of Patent: May 25, 2004

(54) METHOD AND APPARATUS FOR FIXING A LOCATION

(75) Inventors: Christoph Hauger, Aalen (DE); Werner Pöltinger, Oberkochen (DE); Peter Reimer, Ellwangen (DE); Margit Krause-Bonte, Aalen (DE); Theo Lasser, Oberkochen (DE)

(73) Assignee: Carl-Zeiss-Stiftung (DE)

( * ) Notice: Subject to any disclaimer, the term of this patent is extended or adjusted under 35 U.S.C. 154(b) by 140 days.

(21) Appl. No.: 10/034,845

(22) Filed: Dec. 28, 2001

(65) Prior Publication Data

US 2002/0120424 A1 Aug. 29, 2002

(30) Foreign Application Priority Data

Jan. 3, 2001 (DE) .......................... 101 00 335

(51) Int. Cl.$^7$ .............................. G01C 17/00
(52) U.S. Cl. ................ 702/152; 702/94; 702/95; 702/150; 702/153; 600/426; 600/429; 600/407; 606/130
(58) Field of Search ............ 702/94, 95, 152, 702/150, 153; 600/426, 429, 407; 359/393; 606/130

(56) References Cited

U.S. PATENT DOCUMENTS

| | | | | |
|---|---|---|---|---|
| 4,807,987 A | * | 2/1989 | Bastable et al. ............ 351/205 |
| 5,273,039 A | * | 12/1993 | Fujiwara et al. ............ 600/407 |
| 5,359,417 A | * | 10/1994 | Muller et al. ................ 356/623 |
| 5,513,005 A | * | 4/1996 | Muller et al. ................ 356/623 |
| 5,657,128 A | * | 8/1997 | Muller et al. ................ 356/612 |
| 5,697,368 A | * | 12/1997 | Luber et al. ................. 600/407 |
| 5,699,444 A | * | 12/1997 | Palm .......................... 382/106 |
| 5,795,294 A | * | 8/1998 | Luber et al. ................. 600/407 |
| 5,795,295 A | * | 8/1998 | Hellmuth et al. ........... 600/407 |
| 5,867,308 A | * | 2/1999 | Pensel et al. ............... 359/368 |
| 6,004,314 A | * | 12/1999 | Wei et al. .................... 606/12 |
| 6,005,710 A | | 12/1999 | Pensel et al. ............... 359/379 |

FOREIGN PATENT DOCUMENTS

| | | |
|---|---|---|
| DE | 41 34 481 A1 | 4/1993 |
| DE | 42 04 601 A1 | 8/1993 |
| DE | 198 46 687 A1 | 4/2000 |
| DE | 199 30 408 A1 | 1/2001 |
| EP | 0 788 613 B1 | 12/1998 |
| EP | 1 119 306 A1 | 10/1999 |

OTHER PUBLICATIONS

Patent Abstracts of Japan, Publication No:. 2001070317A, Date of Publication: Mar. 21, 2001, 1 page.
English Summary of German Patent Application DE 42 04 601 A1, 1 page.
U.S. patent application No. 09/609,671 entitled "Surgical System Supported by Optical Coherence Tomography", 26 pages.

* cited by examiner

Primary Examiner—John Barlow
Assistant Examiner—Anthony T Dougherty
(74) Attorney, Agent, or Firm—Osha & May L.L.P.

(57) ABSTRACT

A method is disclosed for fixing at least one location in an examination field (9) with respect to a coordinate system (13). The method includes determining, in response to a request (65), coordinates of a first location (59) as a first coordinate set (x, y, z) allocated to the first location (59). A first recording and a second recording of topological data (69) in a spatially extended area around the first location (59) in the examination field (9) are obtained. The first and second recordings are compared to determine a displacement ($\Delta x$, $\Delta y$, $\Delta z$) of the first location (59) of the examination field (9) with respect to the coordinate system (13), the coordinates of the first coordinate set (x, y, z) allocated to the first location (59) are changed dependent upon the determined displacement ($\Delta x$, $\Delta y$, $\Delta z$) such that the changed coordinates substantially correspond to the coordinates of the first location (59) in the examination field (9) after the displacement thereof.

31 Claims, 3 Drawing Sheets

METHOD AND APPARATUS FOR FIXING A LOCATION

BACKGROUND OF THE INVENTION

The invention relates generally to a method and an apparatus for fixing a location in an examination field, in particular in a surgical operating field. In particular, the invention relates also to obtaining data dependent upon the fixed location as well as displaying such data for a user.

U.S. Pat. No. 5,795,295 discloses a surgical microscope comprising an optical coherence tomography (OCT) apparatus with which a surgeon who observes an examination field through the microscope can obtain additional data from the operating field, the data being then displayed on a monitor. Moreover, it is known to obtain additional data from the examination field by means of an X-ray imaging device, an X-ray tomography device (CT) or a nuclear magnetic resonance tomography device (NMR).

In tomography systems known in the art a location within an examination field is fixed or identified, respectively, with respect to a coordinate system. After the location has been fixed, further determinations, examinations or tasks are carried out on the basis of the fixed location. A problem may exist in that the examination field moves relative to the coordinate system, or a field of view of a user observing the examination field moves relative to the coordinate system, so that, after such movement, coordinates of the fixed or identified location are no longer readily determinable.

SUMMARY OF THE INVENTION

One aspect of the invention is a method for fixing the position of a first location with respect to a coordinate system of an examining field. First, coordinates of the location to be fixed in the examination field are obtained as a set of coordinates which is allocated to the location to be fixed. A user identifies the location to be fixed in that the user views the examination field, in certain embodiments, through a microscope and aligns the location with respect to the examination field such that the location to be fixed is positioned in a graticule or in the center of the field of view of the microscope. The user then, in some embodiments, makes a corresponding input to the system which constitutes a request to the system determine the coordinates of the location within the examination field thus positioned in the center of the field of view. The coordinates determined are designated as a first coordinate set. Next, a first recording of topological data is obtained from a spatially extended area close to the identified location within the examination field. After a certain period of time has elapsed, a second recording of topological data of this area is obtained. If the examining field has been displaced relative to the coordinate system during that time, it is possible, by a comparison of the two recordings, to determine the magnitude of the displacement of the identified location with respect to the coordinate system. Next, the coordinates of the first coordinate set are changed, depending upon the determined displacement, such that the coordinates of the first coordinate set substantially correspond to the coordinates of the first location within the examination field after the displacement thereof. It is thus possible to track an identified location within the examination field such that after a displacement of the identified location has occurred, the latter need not be identified again.

In some embodiments, it is advantageous to periodically obtain further recordings of topological data and to determine a current displacement of the identified location with respect to the coordinate system by a comparison of the obtained recordings and to change the coordinates of the coordinate set such that these coordinates indicate the current coordinates of the identified location in the examination field.

In order to identify the location to be fixed, in some embodiments, the user may view the examination field directly, i.e., with the naked eye. In other embodiments, the user may use an imaging device to view the examination field. The imaging device in some embodiments includes a camera and a visual display unit, or a microscope or spectacles, in particular a binocular loupe.

In order to identify the location, in some embodiments a pointer is advantageously provided. The pointer includes a pointer tip which can be contacted by the user at the identified location. Moreover, in such embodiments a position detecting apparatus for determining the position of the pointer tip with respect to the coordinate system is included.

If the user employs an imaging device, some embodiments advantageously include, in addition, a marker which the user may bring into coincidence in the imaging device field of view with the location to be identified in order to identify the same. For example, this marker may be a marking, such as a graticule, which is fixedly positioned in the field of view of the imaging device, or the marker can be displaced by the user in the field of view of the imaging device.

Advantageously, some embodiments include a sightline detecting device or eye-tracker which detects the sightline of the user on basis of an eye position of the user, so that the user can simply identify the location to be fixed by his eye position, i.e., the sightline.

In the embodiments described herein, for the identification of the location to be fixed, the coordinates of the identified location are incorporated in the coordinate set upon a corresponding request made by the user. The user can make this request, for example, by actuating an electrical or mechanical switch, such as a foot-switch, by a voice command or by an eye movement.

After the location to be fixed has been identified, the user may give his attention to other tasks. The identified location is tracked even if it is displaced, in that the coordinate set is changed such that its coordinates substantially correspond to the coordinates of the identified location. In this respect, in some embodiments it is also possible to supply the coordinate set to a data recording apparatus which performs measurements at the location indicated by the coordinate set, i.e., substantially at the identified location, in order to determine at least one magnitude which is correlated with the examination field and is advantageously displayed in the field of view of the user.

Moreover, in some embodiments it is possible to identify, after the first location referred to above is identified, one or more further locations within the examination field and, if desired, to track the one or more further locations as well by means of recordings of topological data and corresponding displacements. An advantageous application of the invention resides in that the determined magnitude incorporates a value which indicates a distance between two identified locations.

Furthermore, in some embodiments it is advantageous for the at least one determined magnitude to incorporate a data set which is obtained from a plurality of measurements performed along a connecting line between two identified locations. This data set may, for example, comprise a depth profile of the examination field taken along the connecting line or a cross-section which is obtained by means of a three-dimensional imaging method, such as computer tomography. In some embodiments, these are advantageously displayed in the field of view of the user as well.

Advantageously, in some embodiments the topological data comprise coordinates of a plurality of surface points within the examination field which are obtainable, for example, by means of laser triangulation or the like. It is also possible to obtain the recordings of topological data by means of a camera, such as a CCD camera, and to compare these recordings to determine the displacement of the location in the examination field.

Moreover, in some embodiments it is also advantageous to use as topological data measuring data which are obtained from points below the surface of the examination field. Such data may, for example, be obtained by means of optical coherence tomography (OCT) or X-ray computer tomography (CT) or nuclear magnetic resonance tomography (NMR) or the like.

A further aspect of the invention provides an apparatus for displaying a magnitude obtained from within an examination field. The magnitude is to be displayed when determined at a location within the examination field which has been previously identified by a user, in the surroundings of such a location or dependent upon such a location. In one embodiment, the user can determine the location to be identified with his eyes by means of a sightline detecting apparatus for determining the eye position of the user. The magnitude to be determined in connection with the identified location is then detected by the apparatus and is displayed in the field of view of the user such that both the display of the magnitude and the examination field as such are in the field of view of the user at the same time. On the one hand, this enables a particularly simple identification of the location in the examination field by the user and, on the other hand, the user can perceive the magnitude measured at the identified location in his field of view without having to turn his eyes away from the examination field, for example, to a conventional display of the measuring value on monitor screen provided outside of the examination field. To this end, in some embodiments the display of the magnitude is advantageously faded into the beam path of a display device such as a microscope or a binocular loupe which the user employs to view the examination field.

In some embodiments, a position detecting device is advantageously provided in order to detect the position of the binocular loupe or the microscope with respect to the coordinate system, so that the coordinates of the location to which the user's eyes are directed can be determined as well by the sightline detecting device.

Other aspects and advantages of the invention will be apparent from the following detailed description and accompanying drawings.

BRIEF DESCRIPTION OF THE DRAWINGS

Embodiments of the invention are described herein below with reference to the accompanying drawings, wherein.

DETAILED DESCRIPTION

Figure 1:
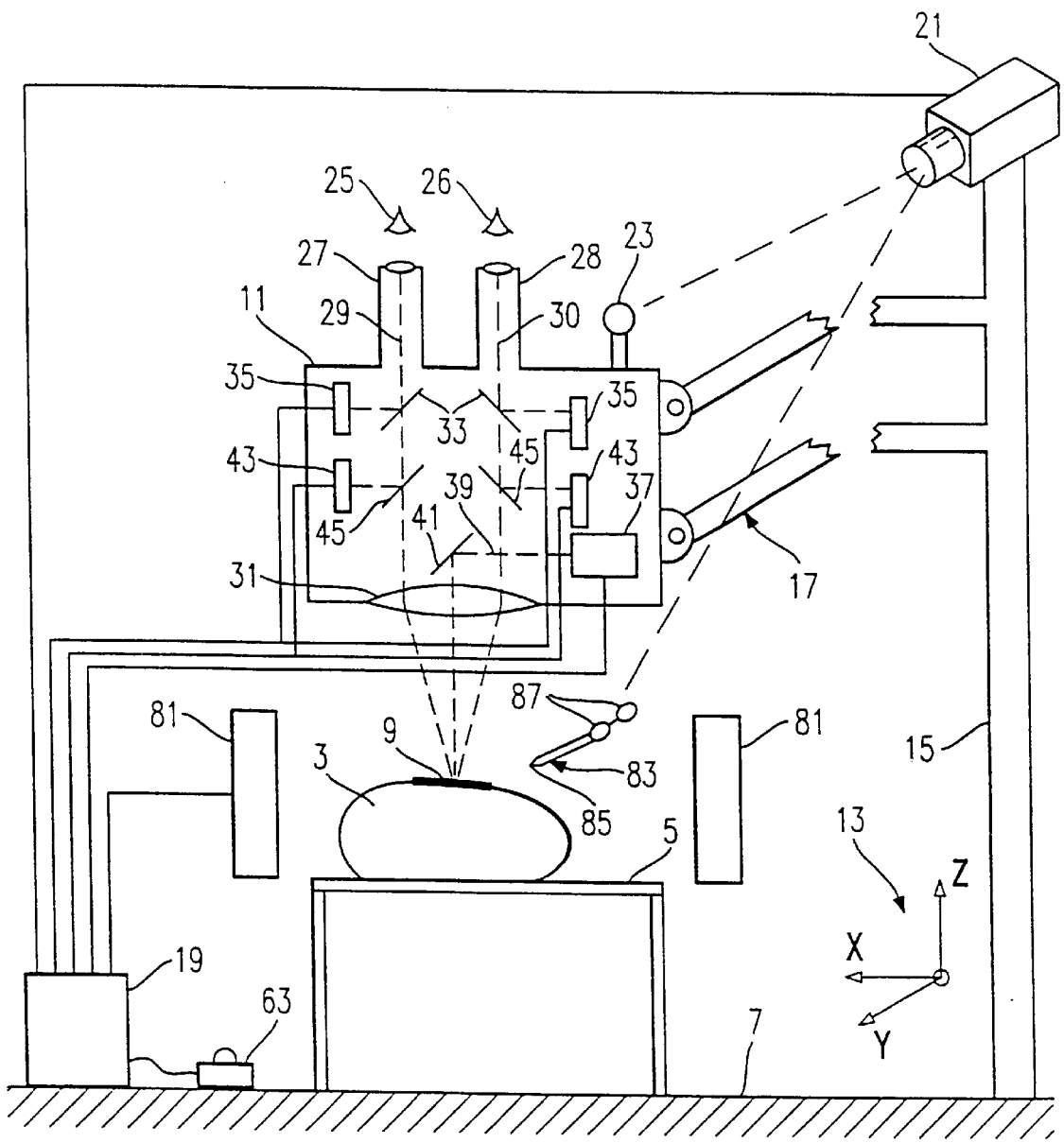
FIG. 1 illustrates a surgical system according to one embodiment of the invention, wherein a user looks through a microscope onto an examination field.

FIG. 1 schematically illustrates a surgical system 1 according to one embodiment of the invention for performing microsurgical operations on a patient. A patient's body part 3 to be operated on is supported on an operating table 5 which is fixedly mounted on a floor 7 of an operating room. An examination or operating field 9 of the body part 3 is viewed by a surgeon through a surgical stereo microscope 11 which is displaceable on a stand 15 by means of a pivot mount 17 in a coordinate reference system 13 of the operating room in the three spatial directions x, y, z. A current position of the microscope 11 within the coordinate system 13 is determined by means of a position detecting device and supplied to a computer 19. The position detecting device in this embodiment comprises a light source 23, such as a light emitting diode, which is fixedly mounted on the microscope 11 and whose position in the coordinate system 13 is detected by three spaced apart cameras, of which merely one camera 21 is shown in FIG. 1. The camera 21 is fixedly mounted on the stand 15.

The surgeon (user) looks with his eyes 25, 26 into ocular tubes 27, 28 of the surgical microscope 11, wherein stereo beam paths 29, 30 allocated, respectively, to the two eyes 25, 26 extend through the two ocular tubes 27, 28 and a common objective lens 31 to the operating field 9 and are focused thereon.

In each one of the stereo beam paths 29, 30, there is positioned a semi-transparent mirror 33 which couples an image of the eye pupil out of the beam path 29, 30 and projects it onto a targeting device, which in this embodiment includes respective one of CCD cameras 35. The image recorded by the cameras 35 are supplied to the computer 19 which analyzes the same and, on the basis of this analysis, determines a sightline of the two eyes 25, 26 of the surgeon (the user). A similar microscope with sightline detection is described in U.S. Pat. No. 6,005,710, the full disclosure of which is incorporated herein by reference.

The surgical microscope 11 furthermore comprises an apparatus 37 for performing topological measurements. In this embodiment, the tomographic apparatus is an optical coherence tomography (OCT) device, the measuring beam 39 of which is optically coupled into the beam path of the microscope 11 via a mirror 41 and focused through the objective 31 in the operating field 9. A microscope including such an OCT apparatus is, for example, disclosed in U.S. Pat. No. 5,795,295, the full disclosure of which is likewise incorporated herein by reference.

Using the OCT apparatus 37, the measuring beam 39 can be scanned and directed to any point within the field of view of the microscope 11 in order to obtain OCT measuring data from the respective points.

Figure 3:
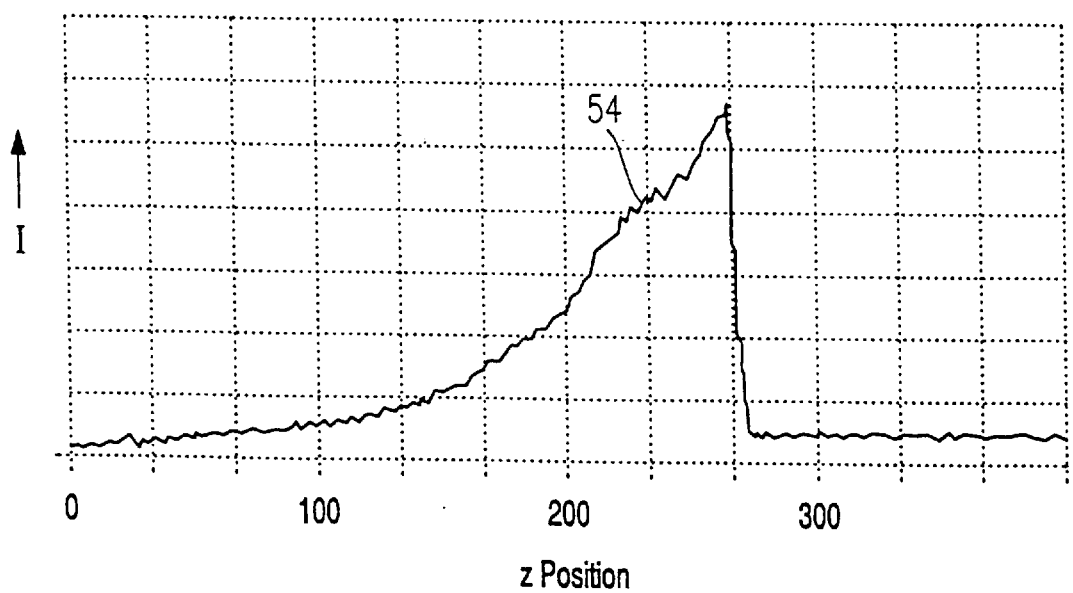
FIG. 3 is a depth profile obtained at a point of the examination field by means of a coherence tomography apparatus of FIG. 1.

One example of such measuring data 54 is shown in FIG. 3, wherein a reflected intensity I of the measuring beam 39 is indicated dependent upon a distance z from the microscope 11. The steep edge at z=265 represents the surface of the body part (3 in FIG. 1) in the examination field (9 in FIG. 1), and the edge descending to lower z values represents the reflected intensity of the measuring beam 39 decreasing dependent upon the depth of the beam within the body part (3 in FIG. 1). The depth of penetration of the measuring beam 39 into the tissue of the body part (3 in FIG. 1) is generally about 2 to 3 mm.

Referring once again to FIG. 1, the OCT apparatus 37 is controlled by the computer 19 such that the location within the examination field 9 where the OCT apparatus 37 obtains its measuring data coincides with the location at which the surgeon (user) looks. The measuring data obtained at this location are again transferred to the computer 19 by the OCT apparatus 37.

The microscope 11 further comprises two LCD displays 43 whose images are respectively optically coupled into the stereo beam paths 29, 30 through semi-transparent mirrors 45, such that they appear in the field of view of the surgeon. An example as to how images are coupled into the beam path of a microscope is also disclosed in U.S. Pat. No. 6,005,710, which patent is incorporated herein by reference.

Figure 2:
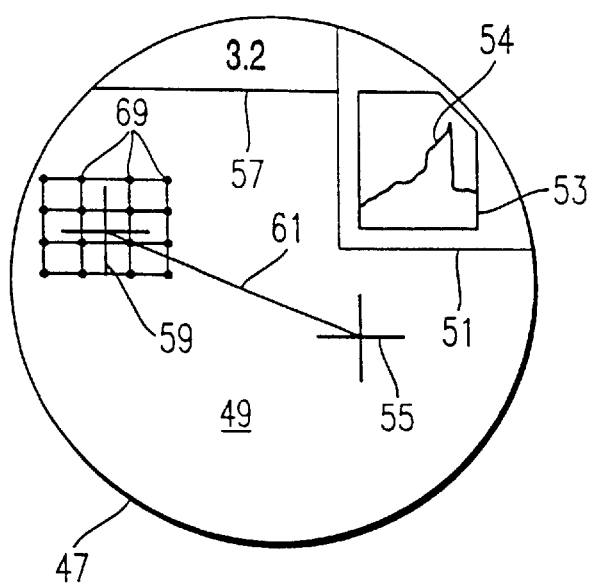
FIG. 2 is a schematic view of a field of view observed through the microscope of FIG. 1.

An example of a representation of a field of view 47 of the microscope 11, as it is perceived by the surgeon (the user), is illustrated in FIG. 2. A partial area 49 of the field of view 47 is provided which remains uninfluenced by the displays 43 for the representation of the operating field 9. The displays 43 produce a representation 53 of the OCT measuring data 54 obtained from the OCT apparatus 37 in a partial area 51 at the right top of the field of view 47. As described above, these OCT measuring data 54 are obtained at the location of the operating field 9 to which the surgeon's (user's) eyes are directed, this location being marked in the partial area 49, for reasons of clarity, by a marking cross 55 which is likewise made visible for the surgeon by the displays 43 in a computer-controlled manner.

The surgical system thus provides a very simple way to obtain OCT measuring data 54 from within an operating or examining field, wherein the locations at which the OCT measuring data 54 are obtained are predetermined by the sightline of the surgeon, and the obtained measuring data are simultaneously displayed in the field of view 47 of the surgeon.

Furthermore, a numerical representation (3,2) of a distance D (in mm) between two different selected locations within the examination field 9, as identified by the surgeon, is faded into a partial area 57 of the field of view 47 of the microscope 11 by means of the displays 43. The two locations whose distance D is faded into the partial area 57 are, on the one hand, the location which is marked by the marking cross 55 to which the surgeon's eyes are currently directed and, on the other hand, a location which has previously been determined by the surgeon and whose position in the field of view 47 is represented by a further marking cross 59 and is faded into the same by the displays 43. Furthermore, a straight connecting line 61 between the two locations 55 and 59 is faded into the field of view 47 by the displays 43.

The identification of the location marked by the cross 59 by the surgeon as well as the display of the position of the cross 59 in the field of view 47 of the microscope are performed in accordance with the method described below with reference to FIG. 4.

The surgeon identifies this location in this embodiment by his sightline and actuation of a foot-switch (63 in FIG. 1). At 65, the system waits for a request to be made by the surgeon (user) by actuating the foot-switch. In response to the request, the system determines, at 67, a coordinate set (x, y, z) of the coordinates of the location in the reference coordinate system (13 in FIG. 1) to which the eyes of the surgeon are directed. Incorporated into this determination are the position of the microscope (11 in FIG. 1) in the coordinate system 13 detected by the position detecting device (21, 23 in FIG. 1) as well as the surgeon's sightline determined by the sightline detecting device (35 in FIG. 1), and a distance of the location to which the surgeon's eyes are directed from the microscope 11, which distance is determined by the OCT apparatus 37.

After the determination of the coordinate set (x, y, z) for the location to be identified by the surgeon, the computer 19 displays this location in the field of view 47 by the cross 59 and, at the same time, at 71, makes a recording of topological data of a spatially extended area around the identified location. The recording of the topological data includes, in this embodiment, OCT recordings of sixteen measuring points 69, which are located around the identified location in the form of a grating, as it is shown in FIG. 2. The points 69, however, are typically not displayed in the field of view 47. As a result, the surgical system 1 obtains knowledge of the topology of the location identified by the surgeon, and is able to track this location, even if the examination field 9 displaces, for example, by respiration movements of the patient (body part 3), or if the surgeon displaces the microscope 11 relative to the patient. Such a displacement can be either or both a translational displacement and a rotational displacement.

Figure 4:
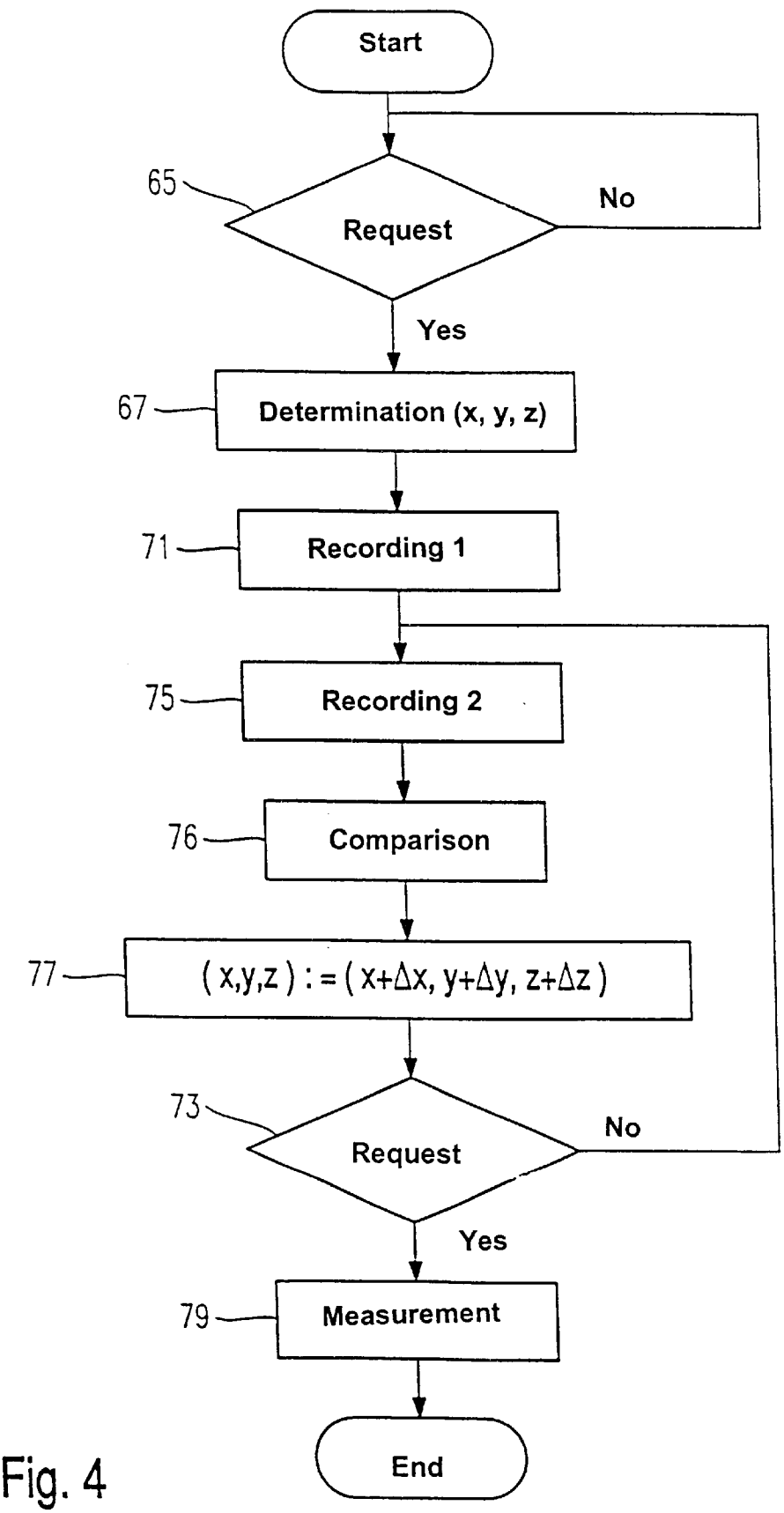
FIG. 4 is a flow chart of the operation of the apparatus according to FIG. 1.

As shown in the flow chart of FIG. 4, the system goes into a loop which is left, at 73, if the surgeon makes a further request via the foot-switch 63. Within this loop, first, at 75, a second recording of topological data is obtained at the same coordinate points 69 in substantially the same way as the first recording was made at 71. At 76, the system compares the two recordings of topological data and, as a result of the comparison, determines a displacement ($\Delta x$, $\Delta y$, $\Delta z$) of the examination field (9 in FIG. 1) with respect to the coordinate system (13 in FIG. 1) which might have occurred in the period of time which has lapsed between the two recordings (between 71 and 75 in FIG. 4). On the basis of this determined displacement ($\Delta x$, $\Delta y$, $\Delta z$), it is possible to determine the coordinates of the location originally identified by the surgeon even after the displacement has occurred, and, at 77, the coordinates of the original coordinate set (x, y, z) are changed accordingly, the position of the marking cross 59 in the field of view 47 being accordingly updated as well.

In order for the desired determination of a distance between two selected locations to be performed, the surgeon can thus first identify the first one of the two locations and can then give his undivided attention to the identification of the second location, because the system automatically tracks the position of the first identified location even if the examination field moves. During the identification of the second location, which is marked in the field of view 47 by the cross 55, the distance from the first location is updated, in some embodiments continuously, within the display area 57 of the field of view 47. OCT or other measurement data of the second location can be likewise constantly faded-in into the display area 51.

If the second location has been fixed to the satisfaction of the surgeon, he actuates the foot-switch 63 again. As a result, the loop referred to above is left at 73 and, finally, a measurement dependent upon the two identified locations (59 and 55) is performed at 79. This measurement may include, for example, an OCT scan along the line 61 between the two locations 59 and 55, a pictorial representation of the corresponding measuring data being faded into the display area 51 of the field of view 47.

In addition, it is also possible to track the second location, at the same time as the first location, according to the method referred to above and explained with reference to FIG. 4, that is, by recording topological data from the area surrounding the second location and by comparison thereof, so that the surgeon may, for example, change the sightline of the microscope (11 in FIG. 1) or perform other tasks before a measurement dependent upon the two locations is carried out. Moreover, after the second location has been identified, still further locations can be identified and measurements dependent upon such additional locations can be carried out.

As an alternative to, or in addition to the OCT scan along the line 61, the measurement performed at the two identified points at 79 can also comprise any other type of data, such as, for example, the performance of an X-ray computer tomography (CT) recording by means of a tomography apparatus (81 shown in FIG. 1), wherein the computer then supplies a cross-sectional representation of the tomography data along the connecting line 61. The tomography apparatus 81 may also be a nuclear magnetic resonance tomography device to supply a corresponding nuclear magnetic resonance tomography (NMR) recording.

The above-described measuring methods provide a representation of a cross-section along the connecting line 61 defined by the two points, the orientation of the cross-section still being selectable in a direction perpendicular to the connecting line 61. Advantageously, this direction, however, coincides with the sightline of the microscope. If, as described above, the second identified point, and thus both points defining the connecting line, are also tracked with respect to displacements in the coordinate system or with respect to the field of view of the observer, it is possible, after the connecting line 61 has been determined, to move the microscope to thus change the orientation of the cross-section and its display in the field of view of the user.

The above-described distance determination by means of the OCT apparatus 37 is advantageously employed in the field of surgeries on the middle ear to measure dimensions of implants, in particular of a stapes prosthesis.

As an alternative to obtaining the recording of topological data at the measuring points 69 arranged in a grating, these measuring points may also be obtained in any other configuration around the identified location 59, such as, for example, at measuring points arranged along a circular path around the identified location.

The recording of topological data can also be effected by methods other than by means of the OCT apparatus 37. For example, the topological data may also be obtained by means of the tomography apparatus 81, or the topological data may also be obtained by means of a camera which is directed to the examination field 9. This camera may also be integrated in the beam path of the microscope 11, for example, in that, just as is the OCT apparatus 37, it is coupled into the beam path of the microscope via the mirror 41.

Moreover, it is possible to use two spaced apart cameras to obtain the topological data, the pictures of which are evaluated photogrammetrically, i.e., utilizing the pictures of the two camera taken at different viewing angles.

If the topological data are obtained by means of a camera, surface data of the examination field are primarily obtained. If use is made of the tomography recording equipment, such as the OCT apparatus 37 or tomography apparatus 81, volume data provided by such equipment are preferably used as topological data.

As described above, the request to identify the location in the examination field is made by the surgeon by actuation of the foot-switch 63. Any other input device is possible as an alternative to the foot-switch 63. To this end, there is in particular provided a voice input device comprising a microphone and a corresponding evaluation program of the microphone signals in the computer 19, so that the surgeon may also make the request by a spoken word. Moreover, it is provided for that the sightline detecting apparatus detects through the cameras 35, for example, an intentional blink of the surgeon's eyes, which is then interpreted by the computer 19 as a request to identify the location. Accordingly, the request can also be made in view-controlled manner.

In the above-specified embodiments, the identification of the location to be fixed via the sightline of the surgeon has been described. As an alternative or in addition thereto, it is also possible to identify the location by means of a pointer device 83 which is held, similar to a pen, by the surgeon in his hand and comprises a tip 85 and two light sources 87 disposed at an end opposite to the tip 85, the position of these two light sources in the coordinate system 13 being detected by the cameras 21. The surgeon can guide the pointer device 83 by hand and approach the tip 85 to the location to be identified. After the request has been made, for example, via the foot-switch 63, the computer 19 then determines the coordinates of the location at which the tip 85 of the pointer device 83 points.

As an alternative to the microscope 11 which is mounted on the stand 15 to be displaceable in respect of the coordinate system 13, the surgeon may also carry a binocular loupe which is secured to his head by means of a support and detects, similar to the microscope, the sightline of the surgeon and fades displays into his field of view via visual display units, the position and orientation of the binocular loupe in the coordinate system 13 being likewise detected by means of a position detecting means. In order to save weight, the apparatus for recording topological data can then be mounted separately from the binocular loupe on a stand in the operating room.

Moreover, it is also within the scope of the invention that the surgeon looks substantially directly at the examination field, i.e., he does not look at the examination field through a magnifying imaging device whose image he views. The surgeon then carries a support for data to be reflected into his field of view so that the reflected data and the examination field are directly in his field of view at the same time. The identification of a location can then be performed in that a marking, such as a graticule, is in the surgeon's field of view and the surgeon moves his head such that the marking points to the location of the examination field to be identified and he then makes the corresponding request. This enables a particularly easy way to identify locations, because a separate sightline detecting device is not necessary. The marking can either be fixedly connected to the support or it can be provided by the data fade-in.

Moreover, in the above-described microscope, or in any other imaging device through which the surgeon looks at the examination field, the marking can also be fixedly connected to the imaging device, so that the surgeon can bring the marking into coincidence with the location to be identified by moving the imaging device and then make the corresponding request.

The invention has been described with respect to a limited number of embodiments. Those skilled in the art, having the benefit of this disclosure will readily devise other embodiments which do not exceed the scope of the invention. Accordingly, the scope of the invention shall be limited only by the following claims.

What is claimed is:

1. An apparatus for fixing at least one location in an examination field with respect to a coordinate system, comprising:

a targeting device for determining a first location within the examination field with respect to the coordinate system and for providing coordinates of the first location as a first coordinate set allocated to the first location;

a topology recording device for obtaining a recording of topological data in a spatially extended area around the first location in the examination field; and means for comparing at least two recordings of topological data, the means for comparing adapted to determine a displacement of the examination field with respect to the coordinate system, the means for comparing adapted to change the coordinates of the first coordinate set depending upon the determined displacement such that the changed coordinates substantially correspond to the coordinates of the first location within the examination field after the displacement thereof, wherein the targeting device comprises a pointer adapted to be moved by a user's hand, the pointer comprising a pointer tip for contacting the first location in the examination field, and a position detecting device adapted to detect the position of the pointer tip with respect to the coordinate system.

2. An apparatus for fixing at least one location in an examination field with respect to a coordinate system, comprising:

a targeting device for determining a first location within the examination field with respect to the coordinate system and for providing coordinates of the first location as a first coordinate set allocated to the first location;

a topology recording device for obtaining a recording of topological data in a spatially extended area around the first location in the examination field; and means for comparing at least two recordings of topological data, the means for comparing adapted to determine a displacement of the examination field with respect to the coordinate system, the means for comparing adapted to change the coordinates of the first coordinate set depending upon the determined displacement such that the changed coordinates substantially correspond to the coordinates of the first location within the examination field after the displacement thereof, wherein the targeting device is adapted to provide coordinates of a second location and a second coordinate set allocated to the second location, and the means for comparing is adapted to determine a distance between the first and the second locations.

3. An apparatus for fixing at least one location in an examination field with respect to a coordinate system, comprising:

a targeting device for determining a first location within the examination field with respect to the coordinate system and for providing coordinates of the first location as a first coordinate set allocated to the first location;

a topology recording device for obtaining a recording of topological data in a spatially extended area around the first location in the examination field;

means for comparing at least two recordings of topological data, the means for comparing adapted to determine a displacement of the examination field with respect to the coordinate system, the means for comparing adapted to change the coordinates of the first coordinate set depending upon the determined displacement such that the changed coordinates substantially correspond to the coordinates of the first location within the examination field after the displacement thereof, a data recording apparatus for recording data at least one point in the examination field determined dependent upon the first coordinate set;

wherein the targeting device is adapted to provide coordinates of at least one further location and at least one further coordinate set allocated thereto, and the data recording apparatus is adapted to record data at a plurality of points which are determined dependent upon the first and the at least one further coordinate set; and wherein the plurality of points are positioned along a substantially straight line between the first and second locations in the examination field as determined by the targeting device.

4. An apparatus for displaying a magnitude obtained from an examination field, comprising:

a sightline detecting device adapted to detect a sightline of a user which is directed to the examination field;

an input device for receiving a request made by the user;

means for fixing at least one location in the examination field with respect to a coordinate system and for providing a coordinate set which is allocated to coordinates of the at least one location in the examination field to which the eyes of the user are directed when the request is received; and a display for displaying at least one magnitude determined dependent upon the coordinate set in the field of view of the user such that the display and the examination field are simultaneously in the field of view of the user, wherein the display comprises a support to be fixedly secured to the head of the user, and further comprising a position detecting device for detecting the position of the head of the user with respect to the coordinate system.

5. The apparatus according to claim 4, wherein the support comprises a binocular loupe, and the display for displaying the magnitude is adapted to be faded into a beam path of the binocular loupe.

6. A method for fixing at least one location in an examination field with respect to a coordinate system, comprising:

determining coordinates of a first location as a first coordinate set allocated to the first location;

obtaining a first recording and a second recording of topological data in a spatially extended area around the first location in the examination field;

comparing the first and second recordings to determine a displacement of the first location of the examination field with respect to the coordinate system;

changing the coordinates of the first coordinate set allocated to the first location dependent upon the determined displacement such that the changed coordinates substantially correspond to the coordinates of the first location in the examination field after the displacement thereof; and determining, in response to a further request, coordinates of a second location as a second coordinate set allocated to the second location, and determining at least one magnitude dependent upon the two coordinate sets.

7. The method according to claim 6, wherein the at least one magnitude includes a value which substantially indicates a distance between the two locations.

8. The method according to claim 6, wherein the at least one magnitude includes a data set obtained from a plurality of measurements taken along a connecting line between the two locations of the examination field.

9. An apparatus for displaying a magnitude obtained from an examination field, comprising:

a sightline detecting device adapted to detect a sightline of a user which is directed to the examination field;

an input device for receiving a request made by the user;

means for fixing at least one location in the examination field with respect to a coordinate system and for providing a coordinate set (x, y, z) which is allocated to coordinates of the at least one location in the examination field to which the eyes of the user are directed when the request is received; and a display for displaying at least one magnitude determined dependent upon the coordinate set in the field of view of the user such that the display and the examination field are simultaneously in the field of view of the user.

10. The apparatus according to claim 9, further comprising a microscope for viewing the examination field by the user, wherein the display for displaying the magnitude is adapted to be faded into a beam path of the microscope.

11. The apparatus according to claim 10, wherein the microscope is displaceable relative to the coordinate system, the apparatus further comprising a position detecting device for detecting the position of the microscope with respect to the coordinate system.

12. A method for fixing at least one location in an examination field with respect to a coordinate system, comprising:

determining coordinates of a first location as a first coordinate set (x, y, z) allocated to the first location;

after the determining, obtaining successively a first recording and a second recording of topological data in a spatially extended area around the first location in the examination field;

comparing the first and second recordings to determine a displacement ($\Delta x$, $\Delta y$, $\Delta z$) of the first location of the examination field with respect to the coordinate system; and changing the coordinates of the first coordinate set (x, y, z) allocated to the first location dependent upon the determined displacement ($\Delta x$, $\Delta y$, $\Delta z$) such that the changed coordinates substantially correspond to the coordinates of the first location in the examination field after the displacement thereof.

13. The method according to claim 1, further comprising:

making a plurality of recordings of topological data;

comparing each of the recordings with a previous one of the recordings;

determining displacements ($\Delta x$, $\Delta y$, $\Delta z$) from each comparison to obtain current coordinates of the first location in the examination field.

14. The method according claims 12, wherein the recordings of topological data comprise coordinates of a plurality of surface points of the examination field.

15. The method according to one of claim 12, wherein the recordings of topological data comprise measuring values of points below the surface of the examination field.

16. The method according to claim 12, wherein the topological data are obtained by at least one of a camera, optical coherence tomography, laser triangulation, X-ray computer tomography and nuclear magnetic resonance tomography.

17. The method according to claim 1, wherein at least one magnitude is determined dependent upon the first coordinate set.

18. The method according to claim 17, wherein a representation of the at least one magnitude is faded into a field of view of a user.

19. The method according to claim 12, further comprising displaying an image of the examination field to be viewed by a user by means of an imaging device.

20. The method according to claim 19, further comprising displaying a marking to be viewed by a user, the position of the marker being displaceable with respect to the examination field as viewed by the user, and determining coordinates of the location of the marker within examination field.

21. The method according to claim 19, further comprising detecting a sightline of the user and determining coordinates of a location within the examination field to which the sightline of the user is directed.

22. The method according to claim 10, wherein the imaging device comprises a microscope.

23. An apparatus for fixing at least one location in an examination field with respect to a coordinate system, comprising:

a targeting device for determining a first location within the examination field with respect to the coordinate system and for providing coordinates of the first location as a first coordinate set (x, y, z) allocated to the first location;

a topology recording device for obtaining, after the first location is determined, a recording of topological data in a spatially extended area around the first location in the examination field; and means for comparing at least two of the recordings of topological data obtained successively, the means for comparing adapted to determine a displacement ($\Delta x$, $\Delta y$, $\Delta z$) of the examination field with respect to the coordinate system, the means for comparing adapted to change the coordinates of the first coordinate set (x, y, z) depending upon the determined displacement ($\Delta x$, $\Delta y$, $\Delta z$) such that the changed coordinates substantially correspond to the coordinates of the first location within the examination field after the displacement thereof.

24. The apparatus according to claim 23, wherein the targeting device comprises a sightline detecting device adapted to provide the coordinates of a position to which the eyes of a user are directed.

25. The apparatus according to claim 23, wherein the targeting device comprises a marking which is adapted to be faded into a field of view of a user, and wherein the targeting device is adapted to provide the coordinates of the first location within the examination field at which the marking points.

26. The apparatus according to claim 23, wherein the topology recording device comprises at least one of a camera, an optical coherence tomography apparatus, an X-ray tomography apparatus and a magnetic resonance tomography apparatus.

27. The apparatus according to claim 23, wherein the data recording apparatus comprises at least one of an optical coherence tomography apparatus, an X-ray tomography apparatus, and a magnetic resonance tomography apparatus.

28. The apparatus according to claim 23, further comprising a display adapted to display data recorded by the data recording apparatus in the field of view of a user such that the display and the examination field are simultaneously visible in the field of view.

29. The apparatus according to claim 23 wherein the means for comparing comprises a computer.

30. The apparatus according to claim 23, further comprising a data recording apparatus for recording data at least one point in the examination field determined dependent upon the first coordinate set.

31. The apparatus according to claim 30, wherein the targeting device is adapted to provide coordinates of at least one further location and at least one further coordinate set allocated thereto, and the data recording apparatus is adapted to record data at a plurality of points which are determined dependent upon the first and the at least one further coordinate set.

* * * * *

UNITED STATES PATENT AND TRADEMARK OFFICE
CERTIFICATE OF CORRECTION

PATENT NO.    : 6,741,948 B2
DATED         : May 25, 2004
INVENTOR(S)   : Christopher Hauger et al.

It is certified that error appears in the above-identified patent and that said Letters Patent is hereby corrected as shown below:

Title page,
Item [73], Assignee, please insert -- trading as Carl Zeiss -- after "Carl-Zeiss-Stiftung".

Column 1,
Line 43, after the word "system" insert -- to --.

Column 4,
Line 24, replace "image" with -- images --.

Column 11,
Line 20, "claim 1" should read -- claim 12 --;
Line 27, please replace "claims" with -- claim --;
Line 39, "claim 1" should read -- claim 12 --; and
Line 56, "claim 10" should read -- claim 19 --.

Signed and Sealed this

Eighteenth Day of January, 2005

JON W. DUDAS
*Director of the United States Patent and Trademark Office*